(12) United States Patent
Wölfert et al.

(10) Patent No.: US 9,061,971 B2
(45) Date of Patent: *Jun. 23, 2015

(54) METHOD FOR PURIFYING RESIDUES CONTAINING ISOCYANATES

(75) Inventors: Andreas Wölfert, Bad Rappenau (DE); Carsten Knösche, Niederkirchen (DE); Matthias Klötzer, Kroppen (DE); Hermann Ascherl, Dirmstein (DE); Eckhard Stroefer, Mannheim (DE); Heinrich-Josef Blankertz, Forst (DE); Michael Schönherr, Frankenthal (DE); Martin Karches, Neustadt (DE); Christian Benz, Worms (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 841 days.

This patent is subject to a terminal disclaimer.

(21) Appl. No.: 12/067,104

(22) PCT Filed: Sep. 21, 2006

(86) PCT No.: PCT/EP2006/066577
§ 371 (c)(1), (2), (4) Date: Mar. 17, 2008

(87) PCT Pub. No.: WO2007/036479
PCT Pub. Date: Apr. 5, 2007

(65) Prior Publication Data
US 2008/0262263 A1    Oct. 23, 2008

(30) Foreign Application Priority Data

Sep. 29, 2005 (DE) .......................... 10 2005 046 816
Oct. 25, 2005 (DE) .......................... 10 2005 051 399

(51) Int. Cl.
| | |
|---|---|
| *C07C 249/00* | (2006.01) |
| *C07C 251/00* | (2006.01) |
| *C07C 257/00* | (2006.01) |
| *C07C 265/00* | (2006.01) |
| *C07C 267/00* | (2006.01) |
| *C07C 291/00* | (2006.01) |
| *C07C 263/20* | (2006.01) |

(52) U.S. Cl.
CPC ........... *C07C 263/20* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 3,405,040 A | 10/1968 | Ewald | |
| 3,694,323 A * | 9/1972 | Cooper et al. | .................. 203/60 |
| 4,216,063 A | 8/1980 | Ailloud et al. | |
| 4,289,589 A * | 9/1981 | Koehler et al. | ................. 203/49 |
| 5,962,728 A | 10/1999 | Mason et al. | |
| 8,088,944 B2 * | 1/2012 | Woelfert et al. | ............. 560/352 |
| 2005/0159495 A1 | 7/2005 | Jennings et al. | |

FOREIGN PATENT DOCUMENTS

| | | |
|---|---|---|
| EP | 0 626 368 | 11/1994 |
| WO | 2004 056759 | 7/2004 |

OTHER PUBLICATIONS

U.S. Appl. No. 12/446,460, filed Apr. 21, 2009, Boehling, et al.

* cited by examiner

*Primary Examiner* — Clinton Brooks
(74) *Attorney, Agent, or Firm* — Oblon, McClelland, Maier & Neustadt, L.L.P.

(57) ABSTRACT

The present invention comprises a process for purifying isocyanate-comprising residues.

17 Claims, No Drawings

METHOD FOR PURIFYING RESIDUES CONTAINING ISOCYANATES

The present invention comprises a process for purifying isocyanate-comprising residues.

In the production of diisocyanates in industry, a predominantly polymeric residue which can still comprise significant proportions of usable product is obtained and needs to be separated off to improve the yield of the process. In addition, the monomeric diisocyanates are usually toxic, so that a content of monomeric diisocyanate in the residue can make it hazardous to handle, for example for disposal.

Depending on the nature of the isocyanate, the residue is solid or forms a highly viscous, sticky and accordingly difficult-to-convey mass.

Processes for separating monomeric diisocyanate from residues from the phosgene process are known in principle.

U.S. Pat. No. 4,216,063 describes a process for separating off monomeric diisocyanate comprising toluene diisocyanate (TDI) whose method of production is not described further, by means of an agitated and self-cleaning evaporator. Under the reaction conditions disclosed (temperature: 70-250° C.; pressure: 1-50 mm Hg), TDI forms a porous, brittle solid which is converted into a flowable material by the milling action of the internals of the vaporizer.

This solution is consequently not applicable to diisocyanates which do not form brittle residues.

EP 626 368 A1 describes a process for separating monomeric diisocyanate from production residues of toluene diisocyanate (TDI), whose production is not described further, with addition of high-boiling hydrocarbons such a bitumen to avoid dust formation. Here too, a flowable product is obtained in a paddle dryer and this can be discharged by means of a transport screw or star feeder. A disadvantage of the process is the need to provide and handle an additional material, namely the high-boiling hydrocarbon, in the plant. Compared to a process which makes do without auxiliaries, there is again increased formation of wastes which have to be disposed of in a landfill or incinerated.

U.S. Pat. No. 5,962,728 proposes, for diisocyanates which form viscous liquid residues, e.g. HDI, IPDI or H12MDI, and which come from a phosgenation process, the use of an evaporative dryer which is divided into a heating zone (temperature: 250-280° C.; pressure: 1-5 mm Hg) and a cooling zone (temperature: 100-120° C.; pressure: 1-50 mm Hg). As a result of the cooling in the downstream cooling zone, the product solidifies in the apparatus to form a brittle solid which, after fine milling, is discharged as a flowable solid by the internals of the apparatus.

A disadvantage of this is that the division into a heating zone and a cooling zone within the apparatus causes start-up problems and in particular leakage problems because of the different expansion. In addition, the energy consumption is increased by the continual heat flow from the heating zone into the cooling zone.

WO 2004/56759 describes the recovery of diisocyanate from residue streams by means of paddle dryers. The diisocyanates can preferably be obtained by phosgenation, but it would also be conceivable for them to be produced by means of a urea process. Diisocyanates are described as "all customary (cyclo)aliphatic and aromatic isocyanates".

A disadvantage of all the abovementioned documents is that they are concerned with diisocyanate production processes based on a phosgenation. The residues from these processes have a significant chlorine content which, firstly, causes corrosion and therefore places severe demands on the material of construction and, secondly, have a completely different by-product spectrum than residues which originate from a phosgene-free process.

A further disadvantage is that the processes disclosed do not differentiate between diisocyanates according to their material properties which make the diisocyanates more or less suitable for recovery.

If solids are formed, these have to be brittle and if viscous liquid residues are formed these have to be converted into a brittle solid.

It was therefore an object of the present invention to provide a process for separating monomers from diisocyanate residues, by means of which the residues can be treated in a technologically simple manner.

This object is achieved by a process for separating monomers from a diisocyanate-comprising residue in at least one apparatus in which the residue forms a high-viscosity liquid and/or a nonbrittle solid during the total residence time in the apparatus at a temperature of from 210 to 330° C. and a pressure below 300 hPa and is discharged from this apparatus by a forced transport means for nonsolid media.

It is an advantage of the present invention that the discharge of the residue which has been depleted in monomer from the apparatus is simplified by means of the selected apparatuses and it is also not necessary for the residue to have to form a brittle solid.

Diisocyanates whose residues can be treated in the process of the invention are preferably (cyclo)aliphatic diisocyanates, particularly preferably diisocyanates having from 4 to 20 carbon atoms. Examples of customary diisocyanates are aliphatic diisocyanates such as tetramethylene diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate, trimethylhexane diisocyanate or tetramethylhexane diisocyanate and cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)-cyclohexane (isophorone diisocyanate), 1,3- or 1,4-bis(isocyanatomethyl) cyclohexane, 2,4- or 2,6-diisocyanato-1-methylcyclohexane and also 3 (or 4), 8 (or 9)-bis(isocyanatomethyl)tricyclo [5.2.1.0$^{2,6}$]decane isomer mixtures.

Among these, preference is given to 1,6-diisocyanatohexane, 4,4'- or 2,4'-di(isocyanatocyclohexyl)methane and 1-isocyanato-3,3,5-trimethyl-5-(isocyanatomethyl)cyclohexane, particularly preferably 1,6-diisocyanatohexane.

Cycloaliphatic isocyanates are isocyanates which comprise at least one cycloaliphatic ring system.

Aliphatic isocyanates are isocyanates which have exclusively isocyanate groups which are bound to straight or branched chains.

For the purposes of the present patent application, the expression (cyclo)aliphatic isocyanates is used as an abbreviation for cycloaliphatic and/or aliphatic isocyanates.

The use of the process of the invention for aromatic diisocyanates is also conceivable, but is less preferred. Examples are methylenedi(phenyl isocyanate) (MDI), tolylene diisocyanate (TDI), naphthylene diisocyanate (NDI) and o-, m- or p-xylylene diisocyanate (XDI).

As monomer-comprising residues to be treated in the process of the invention, it is possible to use the residues of diisocyanates whose monomer-comprising residues form a high-viscosity liquid and/or a nonbrittle solid during the entire residence time within the apparatus under the conditions prevailing there.

For the present purposes, "high-viscosity" means a viscosity of more than 1000 mPas in accordance with DIN EN ISO 3219 under the conditions prevailing in the apparatus.

For the present purposes, the expression "paste-like" refers to a liquid or high-viscosity medium which comprises solids but, in rheological terms, is able to flow under the conditions prevailing in the apparatus but is not able to flow under the sole influence of gravity.

For the present purposes, "brittle" is the property of materials which causes them to break or rupture under load. Brittleness generally appears below a transition temperature $T_t$ above which the material is plastic. Brittle materials are ones which display a steep Hooke's law line in the proportional region of strain and stress in the stress-strain graph obtained when a specimen is loaded with a tensile force F and the resulting length change $\Delta L$ is plotted against it, with the Hooke's law line ending when fracture occurs.

In general, diisocyanates can be obtained industrially essentially either by phosgenation of diamines, e.g. by processes based on the processes described in DE-C 20 05 309 and DE-A 2 404 773, or by phosgene-free processes (dissociation of biurethanes) as described, for example, in EP-B 126 299 (U.S. Pat. No. 4,596,678), EP-B 126 300 (U.S. Pat. No. 4,596,679), EP-A 355 443 (U.S. Pat. No. 5,087,739), EP 566 925 A2 and EP-A 568 782.

In a phosgene process they are prepared by phosgenation of the corresponding diamines and thermal dissociation of the dicarbamoyl chlorides formed as intermediates. Isocyanates originating from a phosgenation process generally have a total chlorine content of 100-700 mg/kg. High-boiling impurities which occur are predominantly chlorine-comprising secondary components.

In phosgene-free processes, also referred to as urea processes, they are preferably prepared by thermal dissociation of the corresponding carbamates. This dissociation is carried out at temperatures of from 150 to 300° C., usually in the presence of catalysts. The diisocyanates and alcohols formed in the dissociation are removed from the reaction mixture and purified, usually by distillation.

Diisocyanates obtained by the latter process have a total chlorine content of less than 80 mg/kg, preferably less than 60 mg/kg, particularly preferably less than 40 mg/kg, very particularly preferably less than 20 mg/kg, in particular less than 10 mg/kg and especially 0 mg/kg.

It is in principle possible to use diisocyanate-comprising residues originating from a phosgene process or from a phosgene-free process in the process of the invention. In a preferred embodiment of the present invention, diisocyanate-comprising residues originating from a phosgene-free process are used.

If diisocyanate-comprising residues-originating from a phosgene process are used, it can be useful make the apparatus at least partly of stainless steel at the thermally stressed regions at which the apparatus is exposed to the chlorine-comprising residue. DIN-EN 10088-1, August 1995 version, defines stainless steels as steels which comprise at least 10.5% of chromium and not more than 1.2% of carbon. Preference is then given to using apparatuses which are made at least partly of austenitic and/or austenitic-ferritic steels in the process of the invention.

Austenitic steels are steels having an austenitic lattice type ($\gamma$ phase) at 20° C. They preferably have a Cr content of from 16 to 28% and an Ni content of from 3.5 to 32%, and also, if appropriate, proportions of S (up to 0.35%), P (up to 0.045%), Mo (up to 7%), Si (up to 4.5%), Cu (up to 4%), N (up to 0.25%) and/or Mn (up to 10.5%) and also possibly Ti (up to 0.7%) and/or Nb (up to 1%). The carbon content is generally below 0.15%. Among these, the high-alloy austenitic 18/8 chromium-nickel steels are particularly preferred.

Austenitic-ferritic steels have a two-phase microstructure comprising ferrite and austenite and having a proportion of ferrite of about 60%. It usually comprises 19-28% of Cr, 3.5-8% of Ni, up to 4.5% of Mo and, if appropriate, proportions of Mn (up to 2%), Cu (up to 2.5%), N (up to 0.35%), W (up to 1%), S (up to 0.015%), Si (up to 1%) and/or P (up to 0.035%). The carbon content is generally below 0.05%.

Very particularly preferred materials are the austenitic and austenitic-ferritic materials described in DIN-EN 10088-1 and especial preference is given to the materials 1.4539 (Falk steel), 1.4541, 1.4571 and 1.4462 and also Hastelloy A and C and zirconium. The specified materials in accordance with DIN-EN 10088 correspond approximately to the following materials in accordance with AISI (American Iron and Steel Institute), UNS (Unified Numbering System), SS (Swedish Standard), AFNOR (Association Francaise de Normalisation), BS (British Standard) and JIS (Japanese Industrial Standards):

1.4462 (X 2 CrNiMoN 22 5 3): UNS: S 31803, SS: 2377, AFNOR: Z 5 CNDU 21.08, JIS: SUS 329 J3L 1.4539 (X 1 NiCrMoCuN 25 20 5): UNS: N 08904, SS: 2562, AFNOR: Z1 NCDU 25.20

1.4541 (X 6 CrNiTi 18 10): AISI: 321, UNS: S 32100, SS: 2337, AFNOR: Z 6 CNT 18.10, BS: 321 S 31, JIS: SUS 321

1.4571 (X 6 CrNiMoTi 17 12 2): AISI: 316 Ti, UNS: S 31635, SS: 2350, AFNOR: Z 6 CNDT 17.12, BS: 320 S 31, JIS: SUS 316 Ti

Among the materials listed, those having relatively high proportions of chromium, copper, molybdenum and/or nickel are advantageous.

In a preferred embodiment of the present invention, the diisocyanate-comprising residue originates from a phosgene-free process.

Simple transfer of residue work-up methods from phosgene processes is not possible, since product streams in phosgene-free processes have a completely different by-product spectrum and consequently also pose different separation problems.

Despite the altered by-product spectrum, the process of the invention not only makes it possible to recover monomeric diisocyanate comprised in the residue but also to redissociate monourethane and/or diurethane and also other usable products comprised therein, so that the effective yield of monomeric diisocyanate in the process of the invention is higher in the case of the residues from a phosgene-free process than in the case of residues from a phosgene process.

A typical phosgene-free preparation is described, for example, in EP 566925 A2, column 6, line 31 to column 8, line 58, which is hereby incorporated by reference.

For the preparation (urethane formation), the diamines corresponding to the diisocyanates are generally reacted with urea and an alcohol, if appropriate in the presence of dialkyl carbonates and/or carbamic esters and if appropriate in the presence of catalysts, at temperatures of from 150 to 300° C. under a pressure of from 0.1 to 60 bar for from 0.5 to 50 hours. Alcohols used are preferably methanol, ethanol or n-butanol. This reaction ideally forms the diurethanes which are dissociated to form the diisocyanates in a subsequent step.

The reaction mixture comprising the diurethanes obtained is then continuously dissociated thermally at temperatures of from 200 to 300° C. and under a reduced pressure of from 0.1 to 200 mbar in the presence or preferably in the absence of solvents in the liquid phase and preferably in the presence of catalysts in a suitable apparatus. The conversion of diurethane to diisocyanate in the apparatus for the thermal dissociation can be chosen essentially freely as a function of the urethane used and is advantageously in the range from 10 to 95% by weight of the amount of urethane fed in.

The undissociated part of the reaction mixture, which comprises unreacted diurethanes, oligourea-diurethanes, high-boiling oligomers and other reusable and unusable by-products, is separated off, discharged continuously from the dissociation apparatus and can be used directly or, if appropriate, after reaction with alcohol in the process of the invention. Such a reaction (reformation of urethane) can be carried out, for example, as described in DE 10338511 A1, paragraph 0033, which is hereby fully incorporated by reference.

The dissociation products formed in the thermal dissociation, which are composed predominantly of alcohol, diisocyanate and partially dissociated urethanes, are then separated, advantageously by means of one or more distillation columns, preferably by rectification at temperatures of from 100 to 220° C. and a pressure of from 1 to 200 mbar, into alcohol and a crude diisocyanate mixture having a diisocyanate content of from 85 to 99% by weight (purification by distillation). The distillation columns generally have from 1 to 50 theoretical plates and are of a construction known per se. The relatively high-boiling by-products obtained in the separation by distillation and in particular the undissociated and partially dissociated polyurethanes can likewise be treated in the process of the invention.

The residues obtained from phosgene-free processes have no chlorine compounds as by-products and therefore possess, as a result of the method of production, a fundamentally different by-product spectrum. In particular, monourethanes and/or diurethanes and also allophanates, biurets and/or uretdiones are comprised as by-products in the residue and can be at least partly recovered according to the invention by thermal redissociation to form diisocyanates in the apparatuses.

An additional advantage of the process of the invention for residues obtained from a phosgene-free process is that there are generally no particular requirements for corrosion-resistant materials, so that the materials from which the apparatus is made do not have to be stainless steels as in the case of residues originating from a phosgene process, but instead the apparatus can be made of normal steel in addition to stainless materials and is preferably made completely of normal steel.

As residue which is fed to the apparatus, it is possible to use, for example, a high-boiler-comprising distillation or rectification residue from the reaction product mixture from diisocyanate formation. Distillation apparatuses are generally operated at from 1 to 80 mbar and at a temperature at the bottom of from 100 to 240° C. The residues are generally obtained as bottom product.

The residues from phosgene-free processes usually comprise not only monomeric diisocyanate but also its polyisocyanates, in particular polyisocyanate comprising uretdione, biuret and/or isocyanurate groups. It is a feature of diisocyanate which has been prepared by a phosgene-free process that the residue also comprises monourethanes or diurethanes, allophanates and/or ureas which can be at least partly redissociated into product of value, in particular monomeric diisocyanate, under the separation conditions used according to the invention.

The content of monomers in the residue depends on the preceding isolation of the diisocyanate. The content of monomers can be up to 90% by weight, preferably up to 80% by weight, particularly preferably up to 70% by weight and very particularly preferably up to 60% by weight.

The monomer-comprising residue which is fed into the apparatus for monomer recovery will in the present text be referred to as "residue" in the interests of simplicity, while the output leaving the apparatus will, for the purpose of making a distinction, be referred to as "residue depleted in monomer".

For the present purposes, the term "apparatus" refers to a process engineering apparatus in which the monomer can be separated off from the residue and subsequently be discharged.

The monomer is separated off from the residue by means of a distillation and/or stripping process; the residue is mixed in the apparatus.

The temperature of the residue within the apparatus is, according to the invention, from 210 to 330° C., preferably from 225 to 305° C., particularly preferably from 235 to 290° C., very particularly preferably from 245 to 275° C. and in particular from 255 to 265° C. As a result of low-boiling constituents being driven off from the residue within the apparatus, the temperature of the residue within the apparatus will generally increase.

The residue can, at particular compositions, tend to foam, and in such an event foam formation commences at a particular lower temperature limit and decreases again at an upper temperature limit. If this is the case, an advantageous embodiment of the invention comprises introducing the residue into the apparatus at a temperature which is above the temperature limit at which foam formation decreases again.

The temperature at which the residue is introduced into the apparatus is preferably more than 120° C. and less than 240° C., particularly preferably more than 150° C. and less than 220° C., very particularly preferably more than 180° C. and less than 210° C.

The pressure within the apparatus is, according to the invention, below 300 hPa, preferably below 200 hPa and particularly preferably under 100 hPa.

The upper residence time limit within the apparatus is generally up to 5 hours, preferably up to 3.5 hours, particularly preferably up to 2.5 hours, very particularly preferably up to 2 hours and especially up to 1.5 hours.

The lower residence time limit within the apparatus is, according to the invention, at least 5 minutes, preferably at least 10 minutes, particularly preferably at least 15 minutes and very particularly preferably at least 20 minutes.

According to the invention, the apparatus has a forced discharging action. Here, the term "forced discharging action" includes the case where the discharge rate of material is increased by structural measures over the natural discharge rate established under the action of the earth's gravity.

In addition, it is useful to configure the apparatus so that it has a forced transporting action and/or a transport gradient for transport of the residue within the apparatus.

For the purposes of the present invention, the term "forced transporting action" means that the residue introduced into the apparatus is moved through the apparatus by introduction of mechanical energy.

The transport through the apparatus has low backmixing or is free of backmixing. These transport characteristics are characterized by a Bodenstein number of at least 3, preferably at least 5, particularly preferably at least 7.

To narrow the residence time distribution in the paddle dryer, the interior space in which product is present is preferably separated into various segments by means of orifice-type plates. Particular preference is given to using at least two plates.

In a preferred embodiment, axial transport through the apparatus is effected by installation of transport, kneading and/or mixing elements, for example disc elements, shafts, screws, blades, wipers or rotors.

A mechanical energy input into the apparatus of 5 W/kg or more is generally sufficient, preferably from 10 or more W/kg, particularly preferably 20 or more, very particularly preferably 40 or more, in particular 80 or more and especially 100 W/kg or more. In general, an energy input of more than 200 W/kg brings no advantages. The specific power input indicated here is the power introduced into the apparatus per amount of residue.

Preference is given to the paddle dryer having forced transport in the axial direction. The forced transport is achieved, for example, by inclination of the surfaces of the transport elements.

Furthermore, it is advantageous for the paddle dryer to have forced cleaning of the interior surfaces which are in contact with product of at least 50%, preferably at least 60%, very particularly preferably at least 70% and especially at least 80%, of these interior surfaces which are in contact with product. The forced cleaning is achieved by the proximity of the transport elements to the outer wall or by the proximity of cleaning hooks to the transport elements.

In addition, not only monomeric diisocyanates but also subsequent products thereof are recovered by means of the process of the invention, as long as they are capable of being separated off and/or redissociated.

In the present text, the term "monomers" is consequently used to refer not only to monomeric diisocyanate but also to its monourethane, diurethane, uretdione, biuret and/or allophanate.

The residual content of monomers in the residue depleted in monomer after the separation is generally less than 20% by weight, preferably less than 15% by weight, particularly preferably less than 10% by weight, very particularly preferably less than 5% by weight and in particular less than 1% by weight.

According to the invention, it can be useful for the monomer not to be separated off as completely as the apparatus would make possible if this would result in the output becoming solid. Instead, it makes good sense according to the invention to leave part of the monomer in the residue depleted in monomer which is discharged from the apparatus in this case, if this results in the residue not becoming solid. This is particularly useful when the savings due to the simplified apparatus more than compensate for the loss of monomers.

In this case, the residual content of monomers after the separation is generally from, for example, 5 to 25% by weight and preferably from 10 to 20% by weight.

To separate off at least part of the monomer comprised in the bottom product before the apparatus, it can optionally be useful to subject the residue to a distillation before it is introduced into the apparatus.

Such a, preferably single-stage, distillation is preferably carried out in a falling film evaporator, a climbing film evaporator, a thin film evaporator, a long-tube evaporator or a helical tube evaporator, particularly preferably in a falling film evaporator.

Such a single-stage distillation is generally carried out at 80-320° C., preferably 100-300° C., and a pressure of 0.1-40 mbar, preferably 0.5-20 mbar.

The diisocyanate-comprising low boiler output from such a single-stage distillation can then preferably be fed to the urethane formation stage and/or purification by distillation.

The residue fed to the apparatus is generally liquid, highly viscous or paste-like, preferably liquid or highly viscous and often has a viscosity at a temperature of 150° C. of up to 500 mPas in accordance with DIN EN ISO 3219.

According to the invention, the process is carried out so that the residue fed in forms a high-viscosity liquid and/or a nonbrittle solid during its entire residence time in the apparatus.

According to the invention, the process is carried out so that the residue leaving the apparatus after being depleted in monomer is discharged without cooling as a high-viscosity liquid, as a nonbrittle, cohesive solid which does not undergo powder flow and is not free-flowing and under pressure can be compacted in a paste-like fashion and/or be plastically deformed and has a yield point of greater than 1 N/m$^2$, preferably greater than 100 N/m$^2$, particularly preferably greater than 500 N/m$^2$.

The advantages of the process of the invention are that the output does not form any dust even without the need to add high-boiling hydrocarbons and residue phases which are not brittle can also be discharged from the apparatus in the process of the invention, so that a cooling zone within the apparatus can be dispensed with.

The density of this output is usually from 500 to 3000 g/l, preferably from 600 to 1000 g/l, particularly preferably from 700 to 900 g/l and very particularly preferably from 750 to 850 g/l.

The apparatuses employed in the process of the invention are apparatuses with forced discharge.

To obtain improved separation of the monomers during passage of the residue through the apparatus, it is preferred that the apparatus has a Bodenstein number of at least 3, particularly preferably at least 5 and very particularly preferably at least 7.

Preferred designs of such apparatuses are
a) paddle dryers without cooling zone and with forced discharge devices,
b) extruders with venting facilities and
c) vertical thin-film processors with forced discharge devices.

a) Paddle Dryers without Cooling Zone and with Forced Discharge Devices

To counter the disadvantage of the prior art, the paddle dryers used according to the invention are not separated into heating and cooling zones, i.e. they have no sudden drop in the temperature by much more than 100° C. as described in U.S. Pat. No. 5,962,728. Instead, the temperature of the residue increases during passage of the residue through the apparatus, preferably with a temperature gradient which changes by not more than 50° C. during passage of the residue through the apparatus and particularly preferably have no significant temperature change during passage of the residue through the apparatus, i.e. less than 20° C. and in particular less than 10° C. As a result, the energy consumption of the apparatus is considerably reduced compared to the prior art and no start-up problems occur as a consequence of separation into a heating zone and a cooling zone.

Such paddle dryers have an essentially horizontal structure, transport of the residue is generally effected by means of one or two mixing and kneading shafts in the interior of the apparatus. In the specialist literature, these apparatuses are also referred to as particle bed reactors, kneading dryers or kneading reactors.

Heating is effected via the wall and can be effected in any way. Heating is preferably effected not only via the outer wall of the apparatus but also via the internals such as cleaning hooks, segmenting plates and kneading shafts.

The thermal energy introduced into the residue via the wall is usually more than 120 kJ/kg of residue and less than 2400 kJ/kg of residue, preferably more than 220 kJ/kg of residue and less than 1800 kJ/kg of residue, particularly preferably more than 300 kJ/kg of residue and less than 1400 kJ/kg of residue and very particularly preferably more than 360 kJ/kg of residue and less than 900 kJ/kg of residue.

The heating section for the residue stream introduced into the paddle dryer preferably makes up more than 10% and less than 70% of the total length of the paddle dryer, preferably more than 20% and less than 60%, particularly preferably more than 30% and less than 50%, of the total length of the paddle dryer.

Such apparatuses are offered by, for example, List AG, Arisdorf, Switzerland, under the trade name Discotherm® B or List-CRP or AP and by Buss-SMS-Canzler GmbH, Butzbach, Germany under the names Reasol® or Reactotherm®.

As discharge devices for forced discharge of the residue depleted in monomer obtained after the monomers have been separated off, which according to the invention is a highly viscous liquid and/or a nonbrittle solid, it is possible to use, for example, screws, preferably twin screws.

Furthermore, the paddle dryer is preferably operated in conjunction with a vapor condenser by means of which the monomer which has been separated off can be recovered.

A preferred embodiment of the present process comprises filling the usable volume of the paddle dryer with residue to an extent of only 25-90%, preferably 30-80%, particularly preferably 40-75% and very particularly preferably 50-70%.

This is advantageous in that a certain degree of foaming of the residue in the apparatus is possible as a result of such incomplete filling.

b) Extruders with Venting Facilities

As an alternative, the monomers can also be separated off in an extruder which is provided with at least one venting facility, for example a degassing dome, via which monomer which has been separated off can be discharged.

For this purpose, the residue is pushed against, for example, an orifice plate or slotted plate under reduced pressure and at the indicated temperature. The kneading in the interior of the extruder results in mixing of the residue so that the monomer is driven off and removed from the extruder via the venting facility. It is then condensed and utilized in a manner known per se.

This alternative is preferred particularly when only small amounts of monomer to be separated off are present in the residue, for example 30% by weight or less.

c) Vertical Thin-Film Processors with Forced Discharge Devices

Such thin-film processors are aligned essentially vertically so that the earth's gravitational field acts as transport gradient for the residue within the apparatus as long as the residue is flowable under the conditions within the apparatus.

Suitable mechanical devices, for example wiper blades, apply and distribute the residue as a thin product film over the heated surface so that the volatile monomer can be separated off.

If necessary, the separation can additionally be aided by passing a gas which is inert under the separation conditions, preferably nitrogen, through the apparatus.

The vapor can be taken off at the top (in countercurrent) or at the bottom (in cocurrent) of the thin-film processor and is subsequently condensed and utilized in a manner known per se.

Vertical thin-film processors allow the residue to be processed, for example, up to a viscosity of up to 15 000 Pas, preferably up to 10 000 Pas, in accordance with DIN EN ISO 3219.

Transport should preferably be aided by shear-optimized rotors so that the wiper blades (rotors) not only produce a thin product film on the heated surface but also forcibly transport the residue within the apparatus. This can be effected, for example, by wiper blades which are inclined in the transport direction.

When the high-viscosity liquid and/or nonbrittle solid residue which has been depleted in monomer after the monomers have been separated off has arrived at the bottom end of the thin-film processor, the natural and the additional transport gradient is generally no longer sufficient to transport it. For this reason, the output is then discharged at the bottom by means of suitable forced discharge systems, for example screws or shafts.

Such thin-film processors are marketed, for example, by Buss-SMS-Canzler GmbH, Butzbach, Germany, under the names Filmtruder® or Viscon®.

This alternative is preferred particularly when large amounts of monomer to be separated off are present in the residue, for example 40% or more.

In all the alternatives, the monomer which has been separated off can, after removal from the apparatus and condensation, preferably be fed to the purification of the diisocyanate. For this purpose, it is combined with a stream from production of the diisocyanate or a stream in the purification by distillation which has a very similar composition.

As an alternative, the monomer which has been separated off in the case of phosgene-free processes can also be recirculated to urethane formation and/or carbamate formation, if appropriate after prior reformation of urethane or reformation of carbamate, i.e. reaction of the monomer which has been separated off with alcohol. A further possibility is to recirculate the monomer which has been separated off to the carbamate or urethane dissociation. In the case of phosgene-free processes, it is therefore preferred according to the invention for the gaseous vapor which has been discharged from the apparatus to be quenched with an alcohol, preferably the alcohol by means of which the monomer is converted into a urethane in the phosgene-free process. This is carried out using an amount of alcohol which is sufficient to bring the vapor into solution or at least suspend it.

Regardless of the method of preparation of the diisocyanate, it can also be useful to recirculate the vapor in gaseous form. For this purpose, it is useful to provide supplementary heating for the recirculation lane in order to avoid undesirable condensation. The temperature is in this case selected so that it is less than or equal to the temperature of the residue in the apparatus used according to the invention and greater than or equal to the boiling point of the isocyanate to be recovered at the selected operating pressure in the gas space.

In an alternative, although less preferred, embodiment, it is possible according to the invention to add at least one additional substance which makes it possible to distill off the monomer more easily and/or leads to a higher viscosity of the output from the apparatus to the residue before or during the treatment in the apparatus.

Such additional substances can be, for example, diphenyl ether/biphenyl mixtures (known as Diphyl), N-methylpyrrolidone, tetradecalin, high-boiling hydrocarbon mixtures, in particular aromatic hydrocarbon mixtures, for example Solvesso® 200 from ExxonMobil Chemical, crystal oil 60: CAS-No. 64742-82-1), heavy solvent naphtha (boiling range about 225-300° C.) or scrubbing oil. The process is preferably carried out without addition of additional substances.

After discharge from the apparatus, the residue which has been depleted in monomer can be disposed of, for example deposited in a landfill or incinerated. Here, the consistency of the residue which has been depleted in monomer outside the apparatus is inconsequential, i.e. solidification and/or embrittlement outside the apparatus is possible without this being a disadvantage according to the invention, as long as the residue does not become brittle within the apparatus.

The invention claimed is:

1. A process comprising:
   separating diisocyanate from a diisocyanate-comprising residue, by way of distillation, in at least one apparatus wherein the diisocyanate-comprising residue forms a high-viscosity liquid and/or a nonbrittle solid during a total residence time in the at least one apparatus, the residue is at a temperature of from 210 to 330° C. in the at least one apparatus, and the at least one apparatus is at a pressure below 300 hPa; and
   discharging a diisocyanate-depleted residue from the at least one apparatus by a forced discharging action of a screw with gravity assistance;
   wherein the at least one apparatus is selected from the group consisting of a paddle dryer without a cooling zone and with a forced discharge device, an extruder with a venting facility, and a vertical thin-film processor with a forced discharge device; and
   wherein the diisocyanate content of the diisocyanate-depleted residue is less than 5% by weight.

2. The process according to claim 1, wherein the diisocyanate is a (cyclo)aliphatic diisocyanate.

3. The process according to claim 2, wherein the (cyclo)aliphatic diisocyanate is selected from the group consisting of 1,6-diisocyanatohexane, 4,4'- or 2,4'-di(isocyanatocyclohexyl)methane and 1-iso cyanato-3,3,5-trimethyl-5-(isocyanatomethyl)cyclohexane.

4. The process according to claim 1, wherein the diisocyanate is obtained by phosgenation of diamines.

5. The process according to claim 1, wherein the diisocyanate is obtained by dissociation of diurethanes.

6. The process according to claim 5, wherein not only monomeric diisocyanate but also its monourethane, diurethane, uretdione, biuret and/or allophanate is separated off.

7. The process according to claim 1, wherein the content of diisocyanate in the residue is up to 90% by weight.

8. The process according to claim 1, wherein the temperature does not change by more than 50° C. during passage of the residue through the at least one apparatus.

9. The process according to claim 1, wherein the diisocyanate-depleted residue leaving the at least one apparatus is discharged without cooling as a high-viscosity liquid and/or as a nonbrittle, cohesive solid which does not undergo powder flow and is not free-flowing and under pressure can be compacted in a paste-like fashion and/or be plastically deformed and has a yield point of greater than 1 N/m$^2$.

10. The process according to claim 1, wherein paddle dryers with forced discharge devices for nonsolid media are used to separate monomeric, (cyclo)aliphatic diisocyanate from residues originating from the production of the (cyclo)aliphatic diisocyanates.

11. The process according to claim 1, wherein extruders having venting facilities are used to separate monomeric, (cyclo)aliphatic diisocyanate from residues originating from the production of the (cyclo)aliphatic diisocyanates.

12. The process according to claim 1, wherein vertical thin-film processors with forced discharge devices for nonsolid media are used to separate monomeric, (cyclo)aliphatic diisocyanate from residues originating from the production of the (cyclo)aliphatic diisocyanates.

13. The process according to claim 1, wherein the diisocyanate content of the diisocyanate-depleted residue is less than 1% by weight.

14. A process comprising:
   separating diisocyanate from a diisocyanate-comprising residue in an apparatus wherein the diisocyanate-comprising residue forms a high-viscosity liquid and/or a nonbrittle solid during a total residence time in the apparatus, the residue is at a temperature of from 210 to 330° C. in the apparatus, and the apparatus is at a pressure below 300 hPa; and
   discharging a diisocyanate-depleted residue from the apparatus by a forced discharging action of a screw with gravity assistance;
   wherein one or more high-boiling hydrocarbons are not added to the apparatus.

15. The process according to claim 14, wherein the diisocyanate content of the diisocyanate-depleted residue is less than 5% by weight.

16. A process comprising:
   adding a diisocyanate-comprising residue to an apparatus,
   separating diisocyanate from the diisocyanate-comprising residue to obtain diisocyanate and a diisocyanate-depleted residue, wherein the diisocyanate-comprising residue forms a high-viscosity liquid and/or a nonbrittle solid during a total residence time in the apparatus, the residue is at a temperature of from 210 to 330° C. in the apparatus, and the apparatus is at a pressure below 300 hPa; and
   discharging the diisocyanate-depleted residue from the apparatus by a forced discharging action of a screw with gravity assistance;
   wherein the weight of the diisocyanate-depleted residue is equal to the weight of the diisocyanate-comprising residue added to the apparatus minus the weight of the separated diisocyanate.

17. The process according to claim 16, wherein the diisocyanate content of the diisocyanate-depleted residue is less than 5% by weight.

* * * * *